United States Patent [19]
Deno et al.

[11] Patent Number: 5,999,854
[45] Date of Patent: Dec. 7, 1999

[54] IMPLANTABLE CARDIAC STIMULATOR WITH PHYSIOLOGIC SENSOR BASED ON MECHANICAL-ELECTRIC PHASE RELATION

[75] Inventors: D. Curtis Deno, Missouri City; Alec Vautravers, Houston; Nicholas F. Pergola, Arvada; Daniel I. Sterling, Houston, all of Tex.

[73] Assignee: Intermedics Inc., Angleton, Tex.

[21] Appl. No.: 09/059,860

[22] Filed: Apr. 14, 1998

[51] Int. Cl.⁶ .................................................. A61N 1/365
[52] U.S. Cl. ............................................................ 607/18
[58] Field of Search ................................ 607/17, 18, 24

[56] References Cited

U.S. PATENT DOCUMENTS 4,773,401  9/1988  Citak et al. ............................. 128/419
5,235,976  8/1993  Spinelli ....................................... 607/5

*Primary Examiner*—William E. Kamm
*Attorney, Agent, or Firm*—Schwegman, Lundberg, Woessner & Kluth, P.A.

[57] ABSTRACT

A cardiac pacemaker includes circuitry which receives a raw impedance signal from the sensor leads of the pacemaker, derives data from the impedance signal that is descriptive of the impedance signal over an entire (or a large part of the) cardiac cycle, develops first order parameters which define that cycle, and provides these parameters to a microprocessor for control of the pacing signal. These parameters may also be used to determine other information about the functioning of the pacemaker. The present invention may also be applied to the determination of tachycardia of an intrinsically paced heart, as well as other applications.

27 Claims, 13 Drawing Sheets

MEP-PHASE FROM TRUE COS/SIN BASIS FUNCTIONS

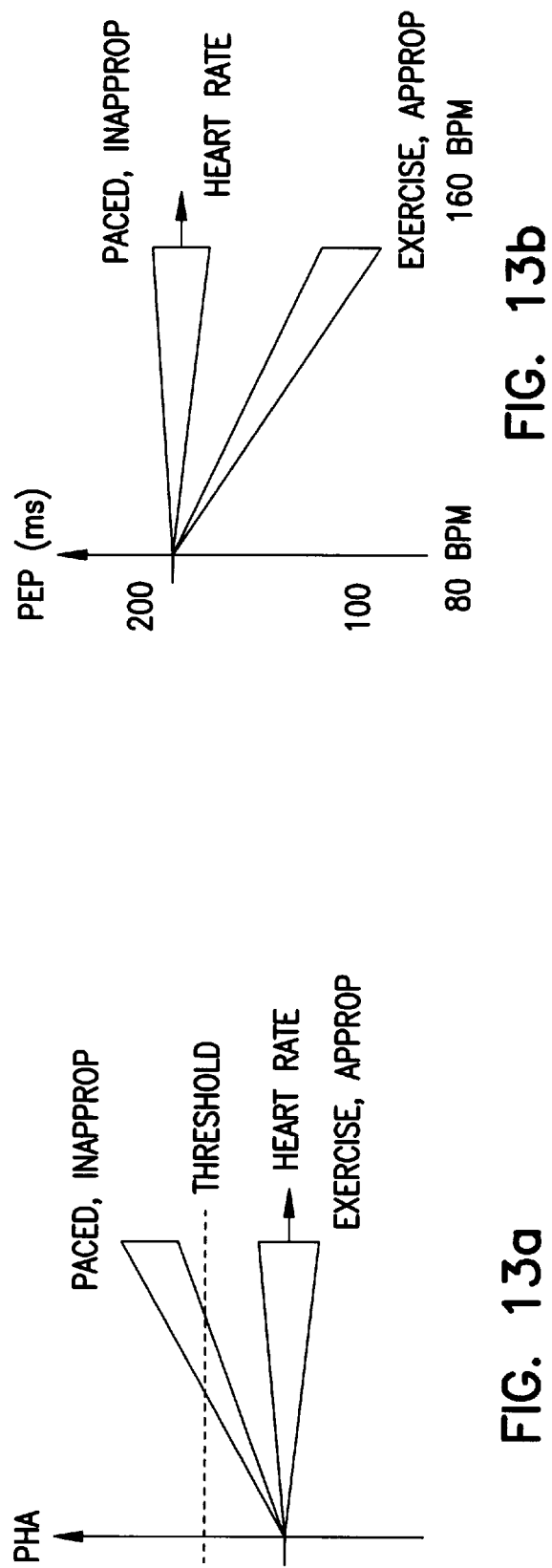

```
    i = 1; j = j +1; % reset indices and accumulators
    T_accum = 0; A_accum = 0; B_accum = 0;
    pa=1; pb = 1; pc = 1;
for k = 1:length(t), % each impedance signal sample
    z(i) = Zproc(k);
    T_accum = T_accum + z(i);
    A_accum = A_accum + 0.50*z(pa);
    if (i - 2*pa == 0), % i was a multiple of 2 {2, 4, 6, ...}
        pa = pa + 1;
    end % if
    B_accum = B_accum - 0.25*z(pc);
    if (i - 4*pc == 0), % i = {4, 8, 12, ...}
        B_accum = B_accum + 0.75*z(pb);
        pc = pc + 1;
        pb = pb + 1;
    elseif (i - 4*pc == -3), % i = {1, 5, 9, ...}
        B_accum = B_accum + 0.75*z(pb);
        pb = pb + 1;
    elseif (i - 4*pc == -2), % i = {2, 6, 10, ...}
        B_accum = B_accum + 0.25*z(pb-1) + 0.50*z(pb);
        pb = pb + 1;
    else, % (i - 4*pc == -1), % i = {3, 7, 11, ...}
        B_accum = B_accum + 0.50*z(pb-1) + 0.25*z(pb);
    end % if
    if (k == idx_Vevent(min(j,NVevent))), % end of cardiac cycle pha = atan2(2*A_accum-T_accum, -(2*B_accum-T_accum));
        if (pha < 0), % enforce 0-360 degrees, 0-2*pi radians
            pha = pha + 2*pi;
        end
        pha = 360*pha/(2*pi);
        mag = sqrt((2*B_accum-T_accum)^2 + (2*A_accum-T_accum^2) / i;
        tim = (pha/360)*cycle_dur;
        i = 1; j = j +1; % reset indices and accumulators
        T_accum = 0; A_accum = 0; B_accum = 0;
        pa = 1; pb = 1; pc = 1;
    else,
        i = i + 1;
    end % if
end % for
```

FIG. 14

IMPLANTABLE CARDIAC STIMULATOR WITH PHYSIOLOGIC SENSOR BASED ON MECHANICAL-ELECTRIC PHASE RELATION

FIELD OF THE INVENTION

The present invention relates generally to the field of cardiac rhythm management devices and, more particularly, to a method and a device for cardiac stimulation based on a measured relationship between certain artificial stimuli and the heart's response to those stimuli, the relationship referred to in this disclosure as mechanical-electrical phase (MEP). This invention further relates particularly to a method and an apparatus which derive characteristics of an impedance signal over an entire cardiac cycle to determine pacing and proper pacemaker function.

BACKGROUND OF THE INVENTION

A variety of cardiac pacemakers have been developed which rely upon measured parameters to control heart rate in order to respond to the level of activity of the patient. A number of these pacemakers seek to eliminate or at least reduce the effects of extraneous or otherwise interfering signals from the desired measured parameter. For example, Deno, U.S. Pat. No. 5,507,785, discloses a rate responsive pacemaker that is sensitive to impedance changes in the heart as an indicator of cardiac stroke volume or minute volume. This pacemaker uses a biphasic test signal to reduce or eliminate common interfering signals from the measurement of the impedance. This pacemaker also includes separate detector and injector circuits so that a variety of electrode configurations may be used.

Other proposed pacemakers are directed to certain measurements that more precisely time the events of interest in the cardiac cycle. U.S. Pat. No. 5,235,976 to Spinelli describes a parameter derived from intracardiac impedance referred to as "total active time". The active time is evaluated using the intraventricular impedance technique, the active time being the length of the interval between the onset of contraction and the point where a line passing through two points on the fast filling segment of the impedance waveform reaches the impedance level corresponding to the end-diastole impedance of the preceding beat. In other words, the impedance signal from the first part of the cardiac cycle is used to derive a minimum (pacing) interval which just accommodates systolic ejection and enough diastolic filling time to support adequate cardiac pump function.

Unfortunately, this technique depends on local (in time) impedance signal characteristics so that additional humps and variations in morphology yields an estimate of total active time that is unreliable. Furthermore, the total active time as determined by Spinelli is not valid for the many cases at high pacing rate when impedance peaks occur after the subsequent pace event.

Spinelli and other techniques also require a high sampling rate to accurately determine crossing times on the impedance waveform. Such a high sampling rate is very demanding of the power source for the pacemaker and therefor reduces the length of time that the pacemaker's installed power source may effectively perform its intended functions. Thus, there remains a need for a cardiac pacemaker that effectively controls cardiac function over a range of demands but requires a much lower rate of sampling the impedance signal over an entire cardiac cycle.

Other proposed solutions are directed to impedance signal processing and certain physiologic sensor implementations. An early example of such a pacemaker is provided in U.S. Pat. No. 4,773,401 to Citak et al. Citak et al. describe a method to determine the pre-ejection period, or PEP, and use this parameter to control pacing. With a few noteworthy exceptions, the resulting parameters of such techniques have not been sufficiently reliable and robust for commercial implementations.

Several factors make the physiologic sensing of heart function by an implantable medical device difficult and thus yield less than robust results. As a result of tradeoffs between size, weight, longevity, and power, as well as mechanical and materials compatibility, the resulting signals reflective of heart function are often contaminated. Artifacts, noise, and variations from one sensor to another and from one subject to another must be artfully dealt with in robust, practical implementations.

One important example of a challenge to the art in sensing heart function is the physiologic determination of maximum pacing rate in response to an activity sensor or paroxysmal atrial tachycardia. Other examples of the difficulties of sensing heart function include tachycardia discrimination and hemodynamic tolerance assessment for ventricular tachycardias and supra-ventricular tachycardias (SVTs), as well as pacing and anti-tachycardia pacing (ATP) capture detection for autothreshold and therapy termination and success evaluation.

Thus, there remains a need for a rate responsive cardiac pacemaker that is more immune to aberrations in sensor output waveforms, including artifacts, noise, and variations from one sensor to another. Such a pacemaker should be robust, should provide robust and reliable responses to the impedance waveform, and should be capable of practical implementation. A sensor must be combined with good signal processing and parameter extraction to assist the medical device to select appropriate therapeutic stimulation. Such a sensor should also be capable of a full range of other therapeutic and analytical functions.

SUMMARY OF THE INVENTION

The present invention addresses these and other drawbacks in the art. A complete understanding of this invention begins with the recognition that the impedance waveform of the cardiac cycle is roughly sinusoidal and that any sinusoidal waveform may be described by its first order parameters of amplitude, frequency, and phase. The second factor in the understanding of this invention is the recognition that changing physiologic or metabolic demand under fixed heart rate and changes of heart rate under fixed demand create changes in the first order parameters, particularly the phase, and thus may signal a need for an alteration in cardiac pacing.

Thus, in the broadest sense, the present invention receives a sensor signal, in a preferred embodiment a raw impedance signal from the sensor leads of a pacemaker, derives data descriptive of the impedance signal over an entire cardiac cycle, develops first order parameters which define that cycle, and provides these parameters to a microprocessor for control of the electrical therapy. These parameters may also be used to determine other intelligence regarding the function of the pacemaker.

It will also be understood by those skilled in the pacemaker and related arts that other physiologic parameters which may be used to develop sensor signals may be effectively used, such as cardiac wall tension or ventricular blood pressure, or other heart motion parameters. As used in this description, impedance signal is used throughout for consistency.

In another aspect, this invention provides a device and a method for robustly deriving physiologic information from implanted pacing lead impedance or other sensor signals. The present invention also provides a broader view of impedance or other sensor applications and signal processing elements desirable in an integrated circuit implementation for future electrogram and other sensor signals. This invention also supplies a robust amplitude measure which, in addition to being useful directly, may also be used to quantify the confidence of the mechanical-electric phase and time parameters.

In yet another aspect of this invention, a sensor sampling and processing system samples a plurality of physiologic parameters of interest over a cardiac cycle by a variety of methods. This related set of parameter extraction methods utilizes a new paradigm—Fourier-like attributes of a sensor signal over a whole (or almost all of) cardiac cycle. This extends parameter extraction in cases like pacing lead impedance in which the sensor signal is insufficiently reliable to utilize either the time at which it (or processed versions of it such as its derivative) meets a threshold criterion or its value at special points in time, such as the minimum or maximum over a cardiac cycle.

The mechanical-electric phase (MEP-phase or simply PHA), time (MEP-time or TIM), and magnitude (MEP-magnitude or MAG) applications of this invention are exceptionally robust statistics which are derived from the impedance waveform over the whole (or large part) of the cardiac cycle. The information extracted is thereby not dependent on detailed wave shape, but rather the computation is spread in time over the cardiac cycle. As a result, noise and moderate sized artifacts such as multiple maxima or minima or ripples during signal rises and falls do not significantly disturb PHA, TIM, or MAG, whereas they can send the pre-ejection period (PEP) and other parameters known in the art to wildly variable values. The process for parameter extraction from sensor signals constitutes a departure from known systems which rely on an impedance signal at a point in time (or, for example, its filtered derivative computed over a narrow time window). Rather, this invention relies on the majority of the signal over a cardiac cycle.

Even when an impedance signal is heavily filtered in order to deal with the uncertainty created by multiple extrema or ripples, conventional point extraction techniques give rise to considerable temporal uncertainty. This problem is fundamental to the determination of extrema because the waveform is flat near a local extremum. To a lesser, but important extent, there remains uncertainty even with threshold crossing time due to waveform variations.

Another important advantage of the MEP parameter PHA is that it is self referenced and that a fixed upper parameter limit may be predetermined independent of subject-to-subject variation. For instance, an upper rate limit might be defined to occur when PHA indicates the peak of the impedance occurs more than 65% into the cardiac cycle.

MEP-phase, MEP-time, and MEP-magnitude may be thought of as "first order physiologic" parameters. Particularly at medium and high cardiac rates, the intracardiac impedance signal resembles a (noisy) sinusoid. Deviations from an idealized sinusoid are not robust within or across subjects, particularly as rate and postures change. The most fundamental first order information is the frequency, phase, and amplitude of the sinusoid, beyond the zero$^{th}$ order information of mean impedance, which is also a byproduct of the MEP procedure of this invention. Frequency is most precisely known from electrogram timing. Phase and amplitude are contained in PHA and MAG, respectively, and TIM is derived from the signal frequency and PHA. PHA is also considered first order in that it may change by 50% of its total range (e.g. 100°–280°) as pacing rates vary from 70 to 140 bpm, whereas PEP may change by 10% or less as rates vary from 70–140 bpm.

Because of the temporally delocalized computation, less low pass filtering of the impedance signal is required. Indeed, little or no filtering is required in most cases. Where lead impedance signals appear variable from cycle to cycle, synchronous averaging (which "smartly" applies FIR or IIR averaging to cardiac cycles of various durations) as disclosed herein provides a resulting signal that is highly usable and fully compatible with the MEP process. Consequences of less filtering include less time delay introduced by causal filters, more prompt parameter estimation, and more rapid response to physiologic changes in the patient. Also, without any other filtering, it recovers from "odd cycle behavior" events like PVCs or posture change induced sudden shifts of impedance by the next one or two beats. This rapid response facilitates outlier removal schemes.

The equivalent of very fine temporal resolution from a high sampling rate is achieved using the MEP method with a reduced sampling frequency. Because of the integrated nature of the calculations, the MEP method distinguishes shifts in MEP-phase and MEP-time beyond the temporal resolution of the sampling rate. This permits less electrical current consumption associated with measurements and processing. In addition, relatively crude 4- to 8-bit AND conversions of impedance have proven sufficient if the baseline offset impedance has been removed.

The MEP method implementations described here are computed in real time from a few, simple logic and arithmetic operations. Such implementations are compatible with low power CMOS IC design from a state machine with a simple register-level interface.

Finally, MEP-magnitude provides a built-in confidence estimate for PHA and TIM. A magnitude value near the sensor's noise floor implies that phase or phase-derived time variables are not accurately estimated. This permits Kalman- or Bayesian-like optimal control implementations which gracefully deteriorate under noisy or low amplitude waveforms as well as less sophisticated Trust-Don't Trust decisions which factor into pacing rate limits or a decision to defibrillate now versus later.

Also, this method of parameter extraction is not restricted to intracardiac impedance but is more broadly applicable to any sensor signal for which first order signal characteristics like the fundamental frequency's amplitude and phase convey more reliable information than classical amplitude or time based parameter estimates.

In another aspect, this disclosure demonstrates the value of this new way to derive physiologic information from sensor signals and applications of these parameters. Important contributions and distinctions from prior impedance signal art include:

(a) a meaningful, inherent signal-to-noise ratio evaluation for confidence in physiologic parameter estimates;

(b) extracted parameters which are tolerant of non-physiologic posture and motion artifacts;

(c) a method which is tolerant of reduced sensor sampling rate;

(d) a method which is tolerant of low signal amplitude resolution;

(e) a "phase" parameter which, unlike pre-ejection period (PEP) or autonomic nervous system (ANS) surrogate signals, is directly useful for physiologic rate limiting and control algorithms;

(f) a rate limit/control parameter that reliably responds to pacing rate before severe hypotension results;

(g) demonstrations of applications which govern pacing rate in response to these extracted parameters;

(h) a parameter of value for assessing if a tachycardia is physiologically tolerated for ICD and pacing mode switching applications; and (i) a parameter useful for reliably confirming mechanical capture by pacing when pacing at times substantially different from anticipated intrinsic times.

Despite the challenges of deriving meaningful physiologic information from pacing and ICD lead electrodes, the task is worthy of special effort. The Thevenin equivalent circuit for implantable electrodes comprises a time varying electrogram source voltage in series with a time varying impedance element. These fundamental sources of information are available from standard pacing and defibrillation leads. Although the "open circuit" electrogram voltage is almost exclusively a result of myocardial depolarization and repolarization, impedance depends on electrode and adjacent tissue geometry and conductivities. The MEP derived parameters of this invention demonstrate superior robustness to posture and motion as well as physiologic significance for rate limiting and control.

A practical implantable device must rely on sensors and extracted parameters which work well, not just in select cases or conditions. Instead, the parameters need to be useful in nearly all subjects and virtually 100% of the time. This follows from constraints that the life saving device is operational 24 hours a day over a period of years. An implementation which is not robust to this level can be expected to exhibit problems which render it substantially useless. The MEP derived parameters, by delocalizing their estimation over most or all of the cardiac cycle, offer independence from nonphysiologic sensor waveform changes. Furthermore, MEP-phase appears particularly well adapted to distinguishing physiologically appropriate from inappropriate tachycardias and physiologically adjusted upper pacing rate limits.

In summary, MEP is a method of processing which is distributed in time and consists almost entirely of a series of simple integer arithmetic and logical operations. MEP computations are compatible with arbitrary cardiac cycle lengths and derive information from the first order information available in the sensor signal's fundamental frequency, amplitude, and phase relative to another timing signal. The three MEP parameters described below include MEP-phase (PHA), MEP-magnitude (MAG), and MEP-time (TIM).

These and other features of the present invention will be apparent to those of skill in the art from a review of the following detailed description along with the accompanying drawings.

BRIEF DESCRIPTION OF THE DRAWINGS

FIGS. 4a–4d depict a Fourier-style MEP analysis of a segment of processed impedance, $Z_{proc}$, along with values of MEP-magnitude and MEP-phase above each cycle in FIG. 4a.

FIGS. 13a and 13b depict symbolic diagrams which capture the essential distinction between the physiologic responses of MEP-phase and PEP, a more conventional time based parameter indicative of autonomic nervous system activity.

FIG. 14 is a segment of computer code for implementing the MEP extraction technique depicted in FIG. 8, which derives PHA, TIM, and MAG from explicit A, B, and T accumulators.

DETAILED DESCRIPTION OF PREFERRED EMBODIMENTS

Figure 1:
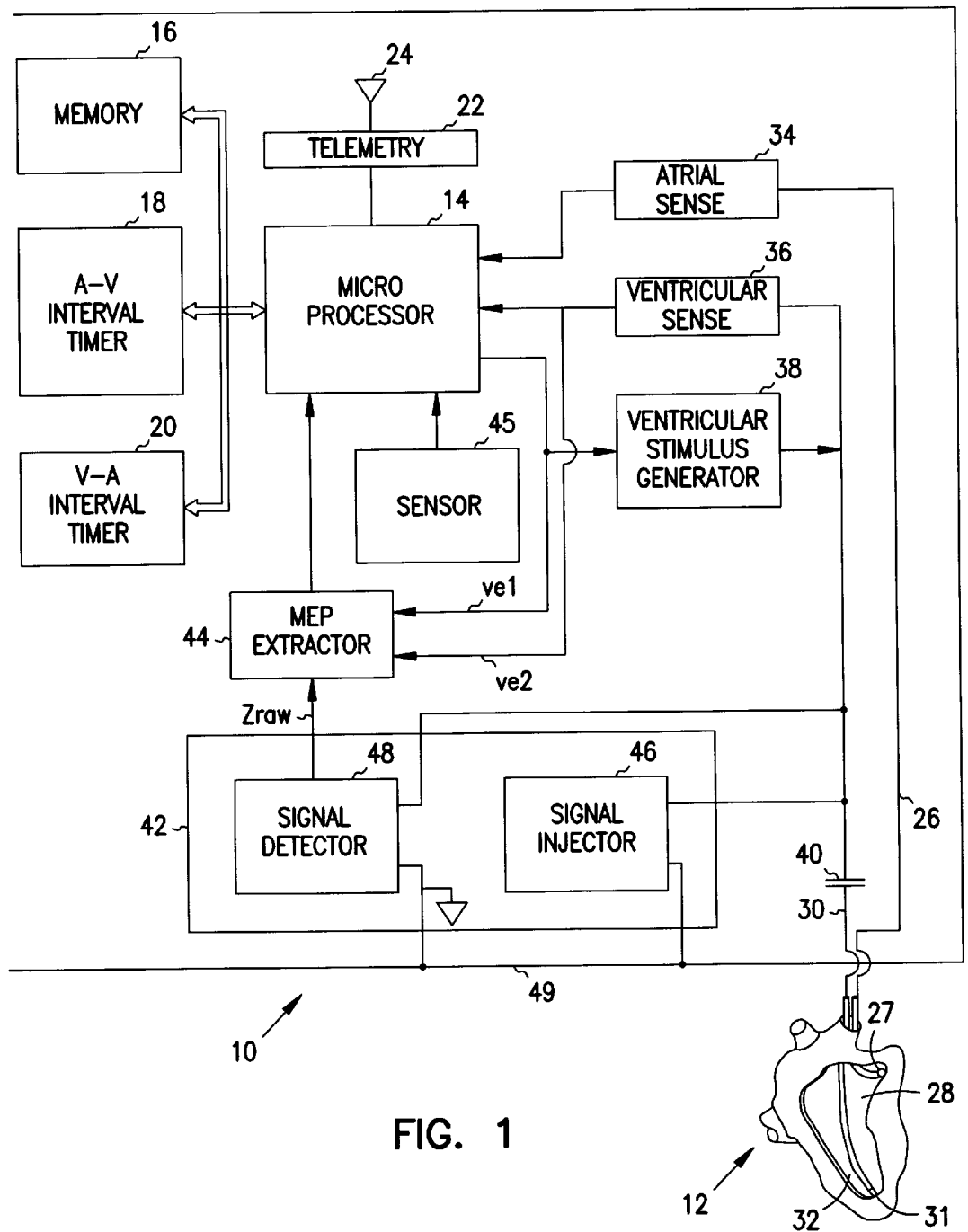
FIG. 1 is a overall schematic diagram of a pacemaker wherein the present invention finds application.

FIG. 1 depicts a pacemaker 10 in schematic form with connection to a human heart 12. The present invention may be used for extracting information from data sensed in the atrium, the ventricle or both; and both atrial or ventricular pacing or either of them may be provided.

The pacemaker 10 comprises a microprocessor 14 which executes various control programs to regulate the action of the pacemaker 10. The microprocessor 14 is connected to a memory 16 for storage of programs and data as needed.

One or more internal clocks may be provided to permit timing of various events. For example, an A-V interval timer 18 and a V-A interval timer 20 may be provided. The microprocessor is also provided with a telemetry circuit 22 so that communication can be provided via an antenna 24 to an external programmer (not shown). Telemetry permits an attending physician to obtain data and information from the pacemaker and to control the pacemaker to set various selectable parameters, as well as other functions known in the art.

The pacemaker 10 is connected to the heart 12 through a first lead 26 to an electrode 27 in the atrium 28 and through a second lead 30 to an electrode 31 in the ventricle 32. An indifferent electrode, such as a pacemaker can 49, is provided to complete the electrical circuit through the body. As shown in FIG. 1, the can 49 or outer casing of the pacemaker serves as the indifferent electrode. Bipolar leads can also be used with this invention as well as the unipolar leads illustrated.

Atrial sensing, through an atrial sense circuit 34, and ventricular sensing, through a ventricular sense circuit 36, provide information to the microprocessor concerning the condition and responsiveness of the heart. Also, pacing pulses are provided to the ventricle from a ventricular stimulus generator 38. Alternatively, atrial or dual chamber pacing may be provided. Stimulation of the heart is passed through a coupling capacitor 40 in a conventional fashion.

To control the pulse rate of the ventricular stimulus generator 38, the microprocessor acquires information on the condition of the heart through an impedance circuit 42. The impedance circuit 42 detects changes in impedance due primarily to the changing shape of the heart as it beats and pumps blood. The shape of the impedance waveform is provided by the impedance circuit 42 to an MEP extractor 44, as described more fully below. It should be understood that the present invention is equally applicable to other time-varying characteristics of the heart.

A sensor 45 may also be provided to obtain an indication of physiologic need and adjust the pacing rate, as described in U.S. Pat. No. 5,507,785 and incorporated herein by reference.

The impedance circuit 42 comprises a biphasic signal injector 46 and a signal detector 48. The biphasic signal injector 46 produces short, essentially symmetrical biphasic constant current pulses to detect the varying impedance of the heart. Each pulse has a duration on the order of 1–50 microseconds and an amplitude of 0.1–2 mA. The resulting voltage seen by the detector will be on the order of 50–1000 mV.

The signal detector 48 is coupled to the lead 30, where it senses the same signal as that provided to the ventricular sense circuit 36 as a varying impedance signal, or $Z_{raw}$. This raw impedance signal is then provided to the MEP extractor circuit 44, which is shown in logic flow form in FIG. 2.

The system shown in FIG. 1 demonstrates the present invention in a two-terminal sensor measuring impedance from the ventricular tip to the indifferent electrode, which in this case is the can. It should be understood that this invention is equally applicable to other two-, three-, and four-terminal sensors as well, and that the two-terminal sensor is illustrated for clarity, although a three-terminal sensor may be preferred.

Figure 2:
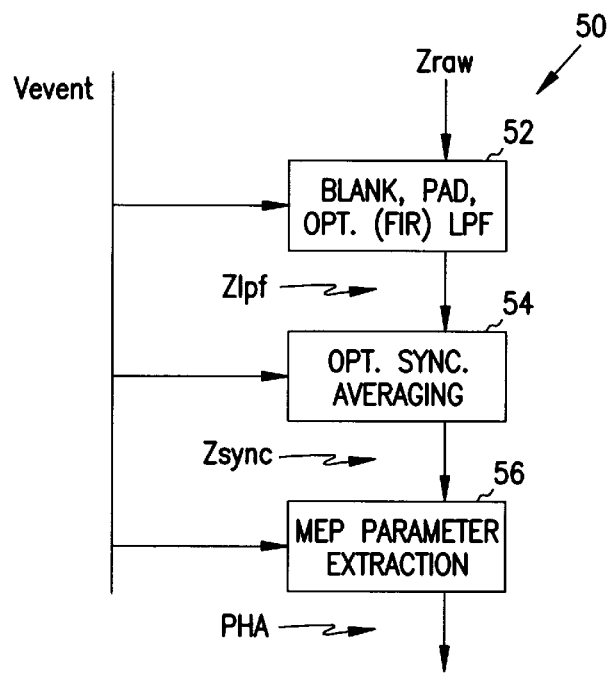
FIG. 2 is a logic flow diagram of the steps of developing an MEP-parameter signal, such as MEP-phase, from the intracardiac impedance signal.

FIG. 2 depicts a logic flow diagram 50 which summarizes the signal processing steps in carrying out the present invention in the MEP extractor circuit 44. FIGS. 3a–3e depict signals throughout the various processing steps of FIG. 2.

Figure 3A:
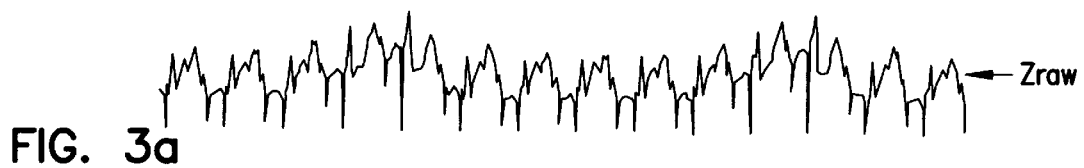
FIGS. 3a–3e depict the various waveforms observed in the steps of FIG. 2.
Figure 3B:
Figure 3C:
Figure 3D:
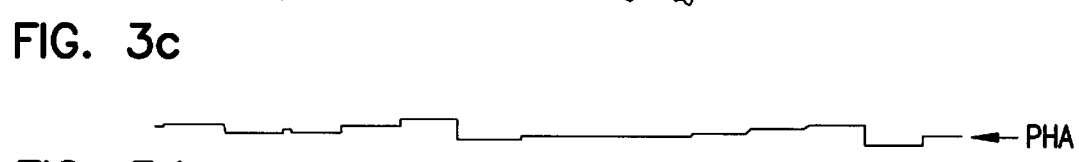
Figure 3E:
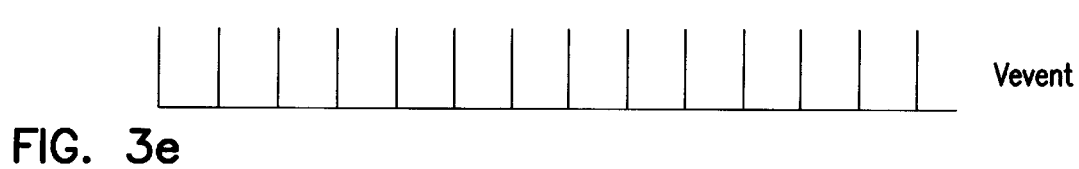

Beginning at the tops of FIGS. 2 and 3a–3e, a raw ventricular impedance sensor signal, $Z_{raw}$ (FIGS. 2 and 3a), is shown with active discharge artifacts from dual chamber pacing. An active discharge artifact is a brief impedance reduction as the residual polarization is dissipated. The next signal, $Z_{lpf}$ (FIG. 3b), has been derived in step 52 from $Z_{raw}$ by blanking the artifacts, padding across them, and low pass filtering. Ensemble or synchronous signal averaging is employed in step 54 to yield the signal labeled $Z_{sync}$ (FIG. 3c). Finally, MEP processing yields physiologic information in the form of the parameter PHA (phase) 56, which is updated once each cardiac cycle as shown in FIG. 3d. This MEP parameter, shown in FIG. 2 as PHA, is then provided to the microprocessor 14. Cardiac cycle boundaries are denoted by $V_{event}$ pulses (FIG. 3e) which coincide with every ventricular pace or sense event.

There are a variety of implementations possible to generate MEP derived information such as PHA (phase), TIM (time), and MAG (magnitude). In common with all of these implementations is a process, distributed in time, consisting almost entirely of a series of simple integer arithmetic and logical operations. Further, the computation is compatible with arbitrary cardiac cycle lengths and derives information from the first order information available in the sensor signal's fundamental frequency, amplitude, and phase relative to a timing signal available to the pacemaker (e.g., a pacemaker or electrogram clock).

Basis Function Projections

Before turning to the preferred embodiments of carrying out this invention as shown in FIGS. 8–11, the following description provides a background on which this invention is based.

Figure 4A:
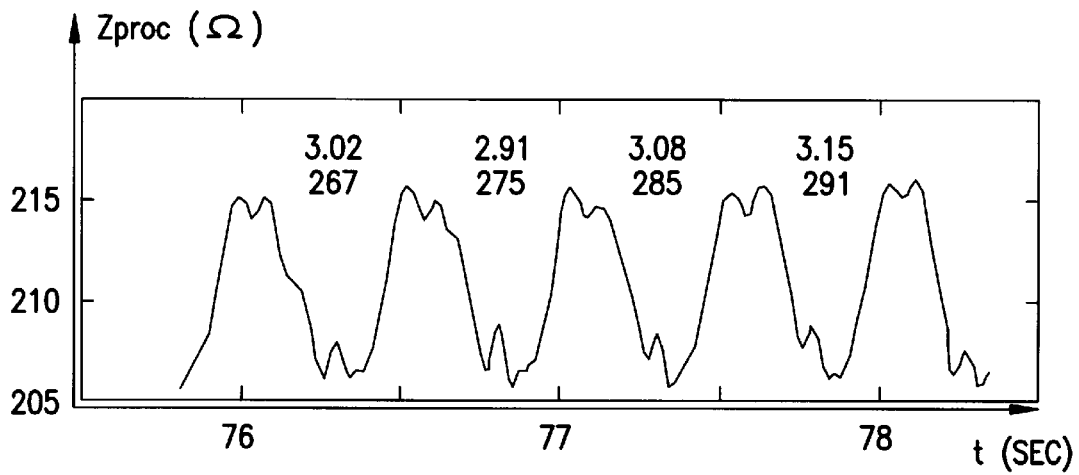
Figure 4B:
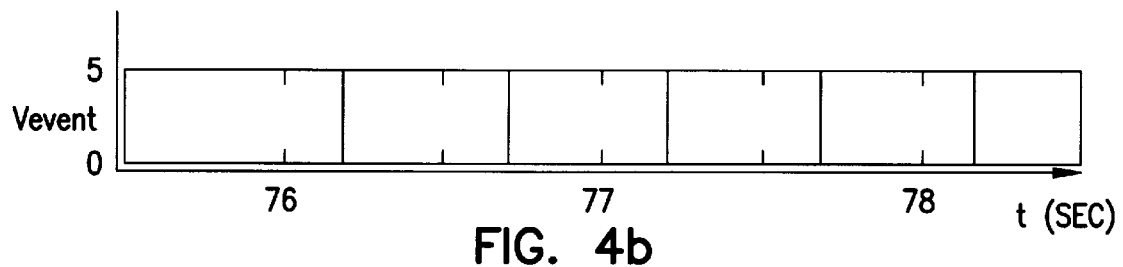
Figure 4C:
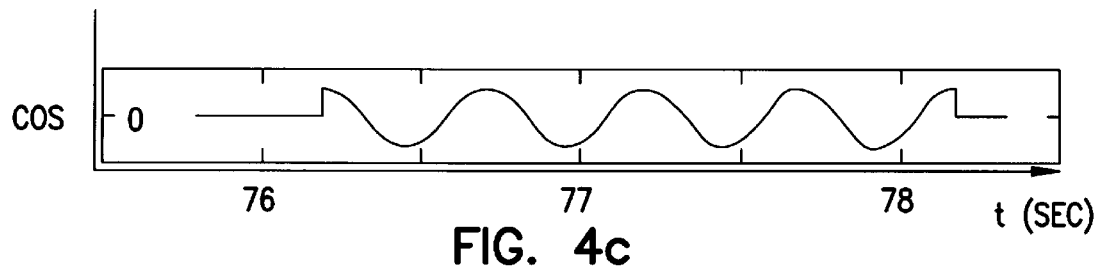
Figure 4D:
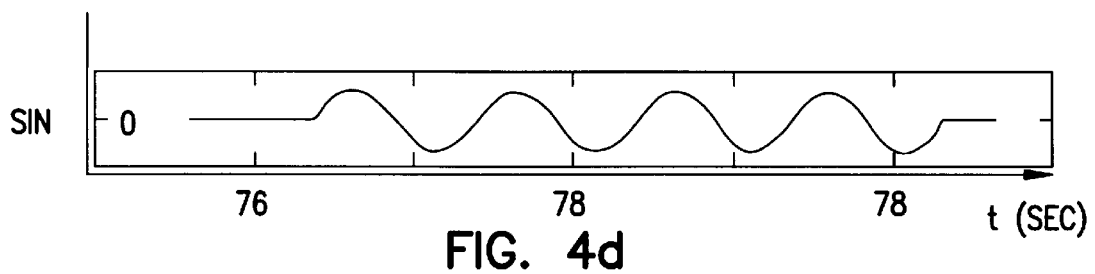
Figure 5A:
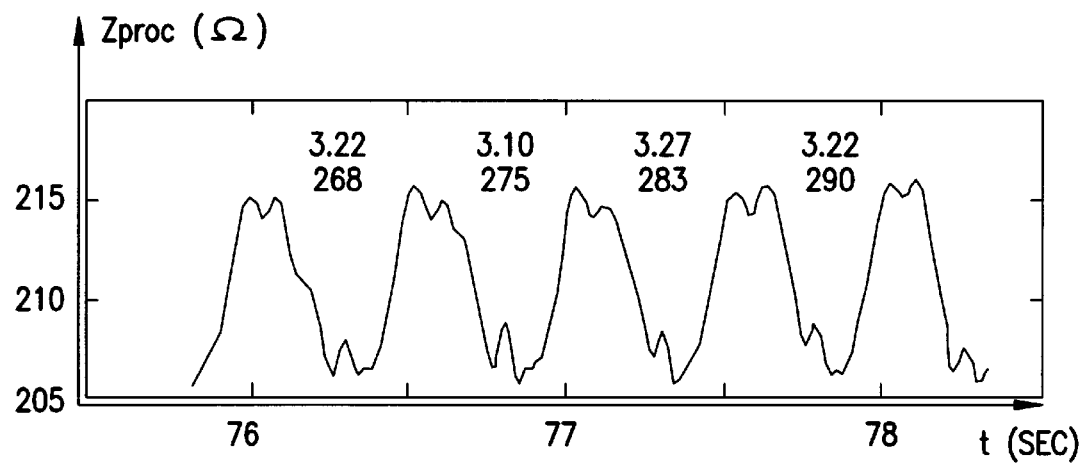
FIGS. 5a–5d depict the sensor signal of FIGS. 4a–4d but with square basis functions, Cosine-Square and Sine-Square and MEP MAG and PHA results in accordance with this invention.
Figure 5B:
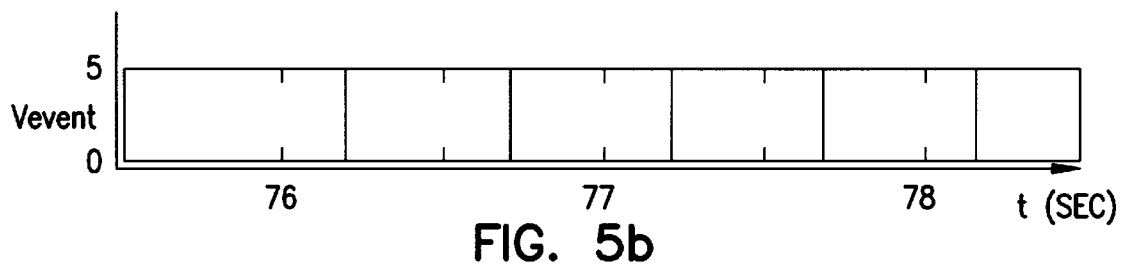
Figure 5C:
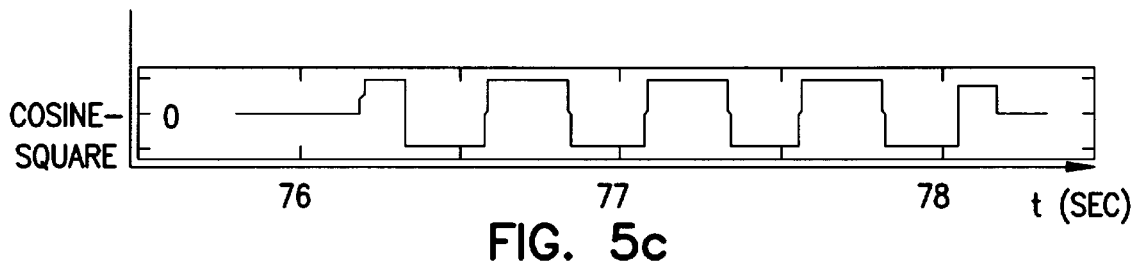
Figure 5D:
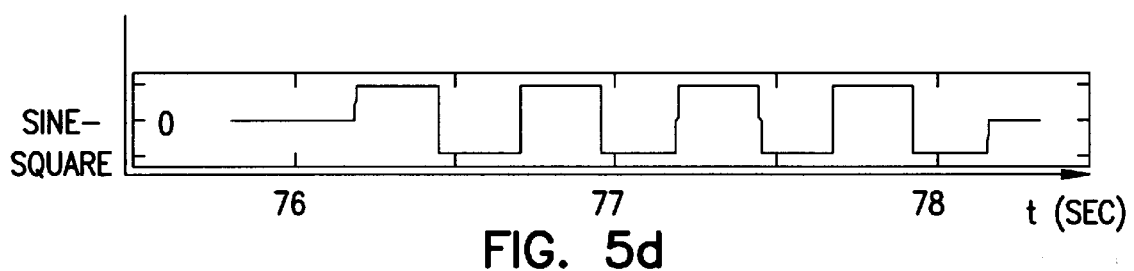

In a manner similar to the Fourier description of periodic signals, fundamental frequency, magnitude, and phase of the impedance signal can be obtained from its inner product or projections onto orthogonal sine and cosine components, as graphically depicted in FIGS. 4a–4d. Although conceptually ideal, the Fourier weighted sums depend on trigonometric sine (FIG. 4d) or cosine (FIG. 4c) functions which in turn depend on the cardiac cycle duration. Between $V_{event}$ markers (FIG. 4b), resulting values for each of four cycles are shown in FIG. 4a for MEP-magnitude (about 3Ω) and MEP-phase (about 280°). The computational burden using this scheme precludes direct integrated circuit implementation in implantable devices.

Instead, piece-wise constant approximations of sine and cosine which adapt to cardiac interval variations are used in the practical implementation in this disclosure. The simplest technique for such an approximation uses two square waves, 90° out of phase and thus orthogonal, instead of sine waves. The result, shown in FIGS. 5a–5d, yields very similar results for magnitude and phase to those of FIGS. 4a–4d.

As used herein, $z_i$ stands for the $i^{th}$ impedance signal sample in a cardiac cycle of length N. The notation Sine-Square refers to the sinewave-like basis function (FIG. 5d), whose values are +1 for the first N/2 samples and –1 for the last N/2. For the embodiments described below, the sine-like square wave requires the summation over the first half of the cycle, A, subtracted from the sum over the last half of the cycle. Similarly, the accumulator B is defined as the sum over the middle half of the cycle. Mathematically, the accumulator values for A, B, and T are defined:

$$A = \sum_{i=1, N/2} z_i \quad \text{(Equation 1)}$$

$$B = \sum_{i=N/4, 3N/4} z_i$$

-continued $$C = \sum_{i=1,N} z_i,$$

although these expressions are strictly correct only when N is a multiple of 4.

Then, the projection or inner product of the sensor signal with the sine-like and cosine-like basis functions are defined:

$$Y = \langle z, \text{Sine-Square} \rangle = \sum_{i=1,N} z_i \text{Sine-Square}_i = 2A - T \quad \text{(Eq. 2)}$$

$$X = \langle z, \text{Cosine-Square} \rangle = \sum_{i=1,N} z_i \text{Cosine-Square}_i = T - 2B \quad \text{(Eq. 3)}$$

Equations 2 and 3 therefore result in values for X and Y projections from which the MEP values may be derived. Further, each of the parameters A, B, and T may be computed in real time with each impedance sample by a simple algorithm implemented in a circuit, such as that shown in either of FIGS. 8, 9 or 14.

At the conclusion of a cardiac cycle, the mean impedance (AVG), MEP-magnitude (MAG), MEP-phase (PHA), and MEP-time (TIM) may be obtained by trigonometric relations $$AVG = T/N \quad \text{(Equation 4)}$$

$$MAG = \sqrt{X^2 + Y^2} / N$$

PHA=atan2(Y,X)

TIM=P(PHA/360°), where P is the cardiac period and PHA is assumed expressed in degrees.

Figure 6A:
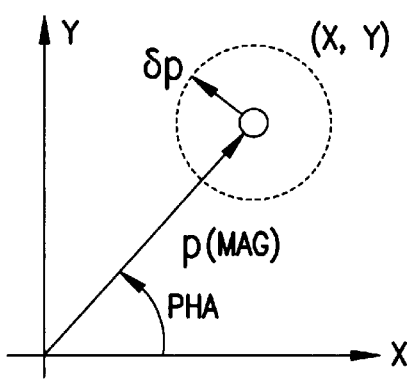
FIG. 6a is a vector diagram depicting the reliability of an MEP parameter in which the MAG parameter is sufficiently greater than non-physiologic noise ($\delta\rho$) and FIG. 6b is a plot of an impedance waveform in such an event.
Figure 6B:
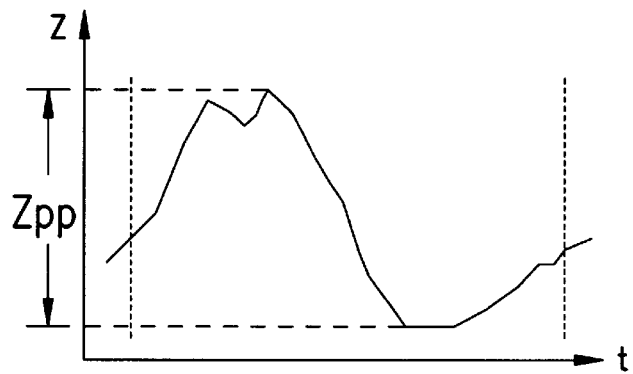

Relationships of certain MEP parameters are depicted in FIGS. 6a and 6b. The region of radius δρ surrounding the coordinate location (X,Y) denotes a region of error or uncertainty jointly in each component which, as long as MAG (of length ρ>>δρ) is relatively large, does not unduly affect the MEP parameters.

Figure 7A:
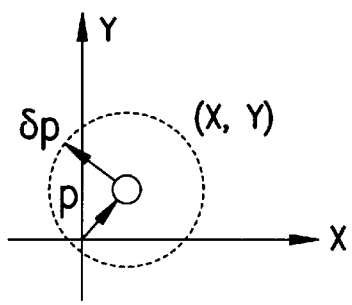
FIG. 7a is a vector diagram depicting the unreliability of an MEP parameter in which the MAG parameter is on the same order of magnitude as non-physiologic noise and FIG. 7b is a plot of an impedance waveform in such an event.
Figure 7B:
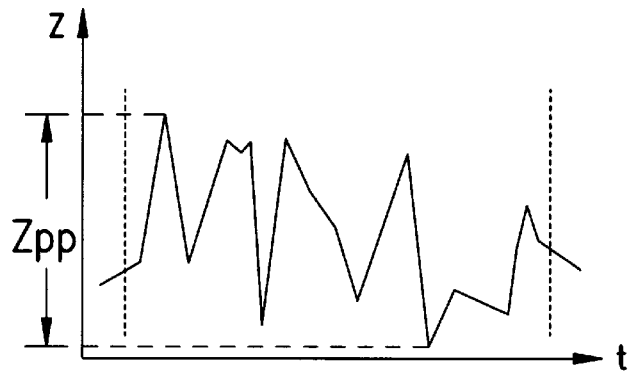

On the other hand, if MAG were comparable to nonphysiologic noise and measurement errors (ρ≈δρ), then MAG and particularly PHA and TIM information is not reliably determined. This may occur despite an adequate peak-to-peak impedance signal level ($Z_{PP}$) as shown in FIG. 7b, comparable to that of FIG. 6b.

Figure 8:
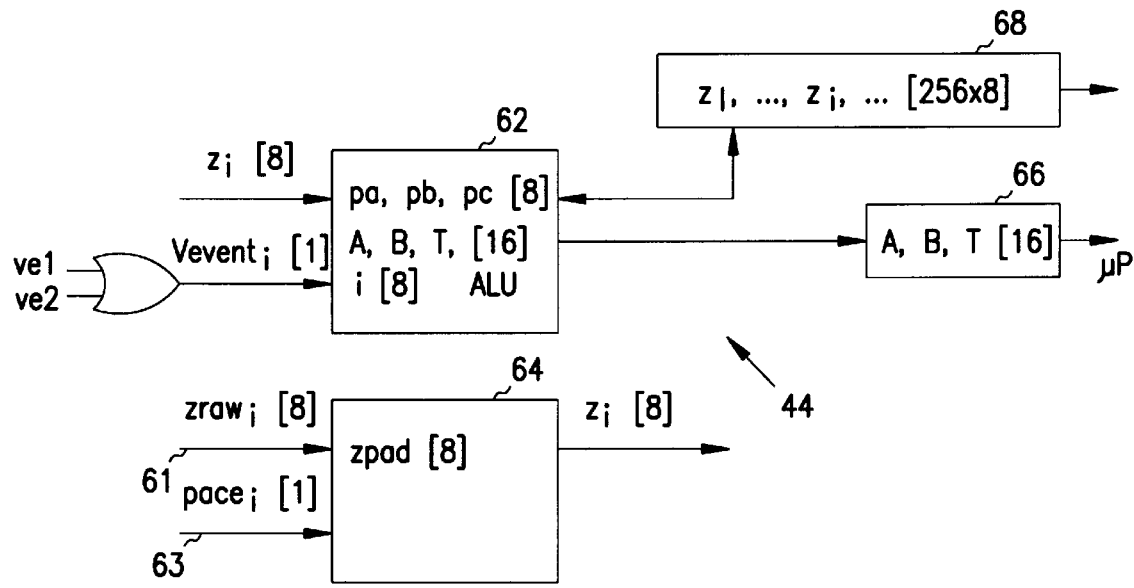
FIG. 8 is a schematic block diagram of a circuit for the extraction of MEP parameters.

The MAG, PHA, and TIM results are independent of slowly varying impedance offsets. This is valuable because physiologic impedance fluctuations are often a small part of the measured impedance and offset correction may be used to better exploit the A/D converter's dynamic range. The implementation of this invention that is depicted in FIG. 8 requires accessing an array of past (8-bit) impedance samples. Such an array can also be used by FIR filter implementations and/or could be part of a synchronous averaging scheme such as the one described in Equations 5 and 6 and FIG. 10 below.

When using TIM as defined by Equations 1–3 above, Equation 4 amounts to a distributed computation of the time of sensor signal peak with respect to the onset of the cardiac cycle. This is superior to a directly determined time to sensor signal maximum for the various reasons described above. Further, depending on the coordinate system, this time could just as well refer to the sensor signal minimum, threshold crossing time such as $PEP_{50\%}$, or a variety of other times. For example, one may define an MEP parameter as follows: MEP-$PEP_{50\%}$=TIM-(P/4).

Again, the MEP derived parameters are superior to the corresponding direct determinations by virtue of their dependence on the entire cardiac cycle's sensor signal.

The MEP Extractor

With this background in mind, now refer to FIG. 8 for a preferred embodiment of an MEP extractor 44. A raw impedance sensor signal 61, $z_{raw}$, is continuously sampled at a fixed rate and fed to a register 64. The unit 64 also provides blanking and padding of asynchronously collected impedance signals to prevent pacing pulse and active discharge interval artifacts from grossly distorting the impedance waveform. This simple implementation does this by padding across the blanking interval by holding the output at its last valid level. Impedance artifacts from atrial and/or ventricular pacing active discharge intervals are eliminated by the unit 64 by using a pace indicator 63 to control whether the output z at point i is the present $Z_{raw}$ or a past value, $z_{pad}$, stored in the register 64. The duration of the padding interval should be slightly longer than the discharge intervals. Thus, the unit 64 develops the output signal, $z_i$.

In the embodiment depicted in FIG. 8, an arithmetic logic unit 62 includes a set of accumulator registers for A, B, and T. The arithmetic logic unit 62 receives the sampled impedance signal, $z_i$, $V_{event}$, and a logically ORed input of $v_{e1}$ and $v_{e2}$. $v_{e1}$ is the microprocessor signal to the ventricular stimulus generator 38 and $v_{e2}$ is the signal from the ventricular sense circuit 36 (see FIG. 1).

The arithmetic logic unit 62 provides the means for MEP processing. The blanked sensor signal z is input to the ALU 62 together with a $V_{event}$ indicator to signal the end of one cardiac cycle and the beginning of the next. An array of sensor signal samples is written to and read from using addresses pa, pb, pc, and i to continuously revise the A, B, and T results in the ALU 62. Upon signaling the end of a cardiac cycle, these results are transferred into a set of registers 66 to be held for the microprocessor 14 to transform into mean, MAG, TIM, and PHA that are used in rate control or rate limiting algorithms.

A sample segment of code for the calculations just described is shown in FIG. 14. Each sample of the sensor signal is read in serially, and the values for the various registers are calculated in real time. Note particularly the technique that is used for corrections for various values for N when N is not a multiple of 4.

Figure 9:
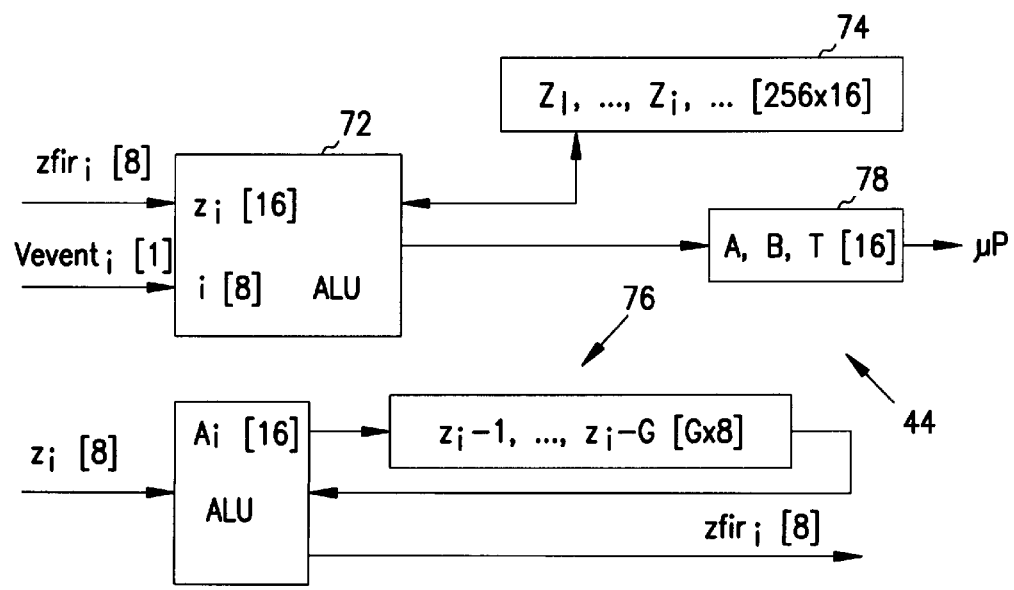
FIG. 9 is a schematic block diagram of another circuit for the extraction of MEP parameters.

FIG. 9 depicts an MEP extractor as an alternative to that shown in FIG. 8 if memory storage is cheap. The MEP extractor 44 may store the array of partial sums $$Z_i = \sum_{j=1,i} z_j$$

in a memory array 74. However, the partial sum array elements $Z_i$ need to be at least 16-bits requiring at least twice as much storage as in the embodiment of FIG. 8. In the case of FIG. 9, the sum for the first half $A=Z_{N/2}$ and the total $T=Z_N$ are read directly from the array 74 (although interpolation is needed to compute A when N is odd). Similarly, the sum over the middle half is $B=Z_{3N/4}-Z_{N/4}$ (again interpolation is required when N is not a multiple of 4). The system of FIG. 9 is preferable to that of FIG. 8 if alternative piece-wise constant basis functions are desired and if the basis functions are to be flexibly determined by software.

Referring again to FIG. 9 and beginning with a blanked sensor signal z at the bottom left which may be developed in manner similar to that provided by unit 64 in FIG. 8, a low pass filtered version, $z_{fir}$, is produced by a simple boxcar type FIR filter 76. For each sample, the accumulator A is increased by $z_i$ and decreased by $Z_{i-G}$ (after A has been initialized correctly) and then $Z_{fir}=A/G$. Optionally, this low pass filtering step may be omitted.

The MEP computation of A, B, and T is performed by the ALU 72. For each new signal sample, $z_{fir}$, the cumulative sum variable Z is increased and stored in an array 74. Upon the $V_{event}$ indicator asserting that the cardiac cycle consisting of N events has just ended, up to 6 values are read from this array; interpolation is performed to yield the cumulative sums at N/4, N/2, and 3N/4; and then A, B, and T are computed and stored in a set of registers 78. As before, the values A, B, and T are then provided to the microprocessor for the development of the MEP extraction parameters.

Synchronous Averaging

Figure 10:
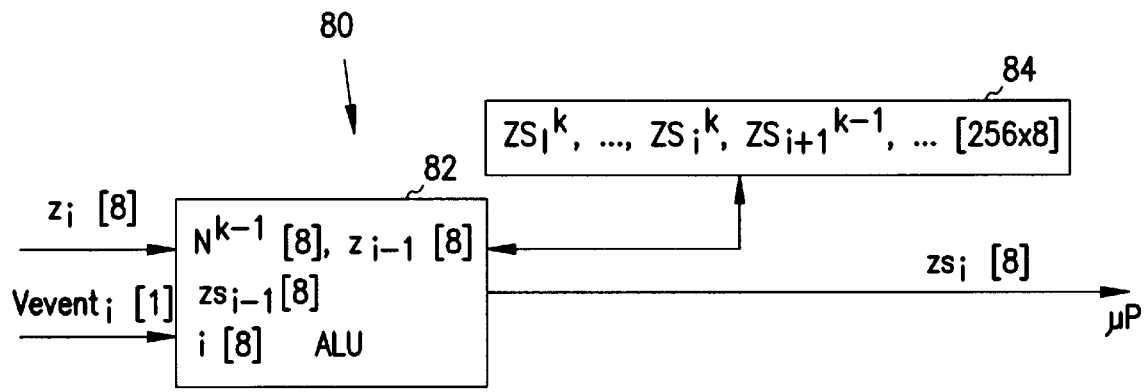
FIG. 10 depicts a synchronous averaging circuit for ventilatory and other artifact suppression by specialized low pass filtering.

FIG. 10 depicts a circuit 80 for specialized low pass filtering and ventilatory artifact suppression known as synchronous averaging. The output of the circuit is immediately compatible with MEP extraction described above. The synchronous averaging circuit 80 is useful in regularizing and cleaning cardiac cycle fluctuations by suppressing perturbations peculiar to specific cycles. The parameters derived from such signals are thus inherently low pass filtered and the resulting improved parameter stability has led to more robust rate limiting and control applications. For some extremely "noisy" sensor signals, such as the top signal of FIG. 12, the result is a dramatic improvement for the synchronous averaged signal.

The $V_{event}$ indicator, fed to an ALU 82, initializes an array index i at the start of each cardiac cycle. For each new signal sample within a cardiac cycle k, the prior synchronously averaged output at index i (from cycle k−1) is blended with $z_i$ in a convex combination to make a 1-pole IIR low pass filter:

$$zs_i^k = \begin{bmatrix} \alpha zs_i^{k-1} + (1-\alpha)z_i^k, & \text{if } i \leq N^{k-1} \\ z_i^k + (zs_{N^{k-1}}^k - z_{N^{k-1}}^k), & \text{else} \end{bmatrix} \quad \text{(Equation 5)}$$

or equivalently $$zs_i^k = \begin{bmatrix} \alpha zs_i^{k-1} + (1-\alpha)z_i^k, & \text{if } i \leq N^{k-1} \\ z_i^k - z_{i-1}^k + zs_{i-1}^k, & \text{else} \end{bmatrix} \quad \text{(Equation 6)}$$

Alternatively, an FIR low pass filter blend may be used but requires additional memory storage for past cardiac cycles.

The values thus derived are stored in an array 84. If the present index extends beyond the end of the last cardiac cycle, $N^{k-1}$, the circuit 80 depends on only the present sensor signal in the present beat, $z_i^k$. The terms $(zs_{N^{k-1}}^k - z_{N^{k-1}}^k)$ and $(-z_{i-1}^k - zs_{i-1}^k)$ are offset corrections to splice cleanly with the synchronously averaged signal. In practice, one should choose $\alpha = p/m$ and m to be a power of 2. A good choice for flexibility and function is m=8 and p in the range of 4 through 6.

Ventilation and Baseline Drift Removal Extension to MEP Calculations

Ventilation related variations of the impedance baseline over a single cardiac cycle induce small errors in the MEP parameters. The MEP extraction methods and structure previously described both permit simple linear "detrending" corrections. For example, if a cardiac cycle of N sensor samples ended $d=z_N-z_1$ apart, one may correct the A, B, and T accumulators by $$T^* = T - 1/2Nd \quad \text{(Equation 7)}$$
$$A^* = A - 1/8Nd$$
$$B^* = B - 3/8Nd$$

Low Pass Filter and Comparator

Figure 11:
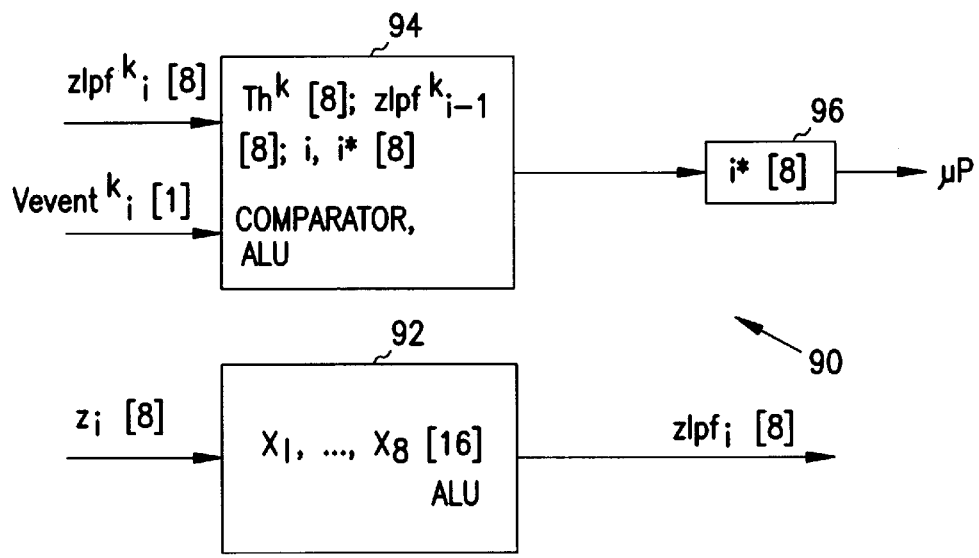
FIG. 11 depicts a circuit diagram for low pass filtering of the sensor signal to coerce it into a sinusoid at the fundamental frequency so that the signal is readily converted into MEP time, TIM.

FIG. 11 depicts an alternative, although not the preferred, implementation of this invention which relies on IIR or FIR low pass filtering of the sensor signal to coerce it into a sinusoid at the fundamental frequency. Once this is done, any fiducial point of the resulting sinusoid (such as time-to-max or better, or the time to 50% of the way down from max to min) is readily converted into MEP phase or time as previously described. However, this approach has certain drawbacks:

(a) the original signal's magnitude is reduced by the strong low pass filter attenuation to a variable extent dependent on the heart rate;

(b) this embodiment requires a multirate or large order FIR filter or an IIR filter with high precision internal states to achieve the strong low pass filtering required for sufficient accuracy;

(c) ventilation and baseline drift compensation as described in Equation 7 above are not possible;

(d) the reduced amplitude of the signal makes the determination of time and phase angle less accurate;

(e) the time delay introduced by causal low pass filters generates an artificial coupling of heart rate to PHA and TIM which is particularly objectionable at high rates and requires compensation;

(f) this embodiment cannot capitalize on the benefits of coherent or synchronous signal averaging such as given in Equations 5 and 6; and (g) this embodiment cannot decrease the sampling rate to below the resolution needed for direct determination of times.

FIG. 11 depicts a diagram for implementing this method of heavy low pass filtering and slope/level triggering. The result is i* the last time during cardiac cycle k that (for example) $zlpf_i^k > Th^{k-1}$ and $Zlpf_{i-1}^k \leq Th^{k-1}$, where threshold $Th^{k-1}$ is the mean of $z_{lpf_i}$ over cardiac cycle k−1. If the phase delay associated with the low pass filter for cardiac frequencies is c samples, then under these assumptions PHA=360°× ((i*−c)/$N^k$+¼).

The regularly sampled, blanked, and padded impedance signal may be filtered by cascading two 4-pole IIR filters, each of which operate with extended precision multiply and accumulates due to the disparity between sampling rate and cutoff frequency, in an ALU 92. Alternatively, multirate FIR filters may be cascaded. The low pass filtered signal, reduced to its cardiac fundamental frequency component, is used as input to a slope and level comparator 94. The resulting i* is stored in a register 96 for transfer to the microprocessor.

Causal Filter Time Delay Compensation Extension

If causal filtering is performed on the sensor signal, it will delay this signal with respect to the clock or electrogram timing reference. The filter's time delay may be defined as Δ seconds or c samples. This delay will provide an additional but nonphysiologic phase to cycle k's MEP-phase, $PHA^k$. The extent of this increase depends on the duration of that cycle, $D^k$ seconds or $N^k$ samples. This artificial relationship of MEP-phase to rate may be removed by $$\begin{cases} PHA^k - 360° \times (\Delta/D^k) \\ PHA^k - 360° \times (c/N^k) \end{cases} \quad \text{(Equation 8)}$$

If the relative contribution to phase is small, say less than 20° at the higher heart rates, then this correction may be neglected. Experience has shown, however, that this correction is necessary when applying significant low pass filtering to cardiac impedance signals.

The distributed nature of computations in MEP derived parameter extraction gives rise to significant advantages in the minimum sensor sampling frequency and sampling resolution required. Experience has shown that reducing the impedance sampling frequency has not degraded the performance of this invention. Rather, the MEP extraction parameters that result from the lower sampling frequency are essentially identical to those using a high sampling frequency. The same result has been found for a lower signal level resolution. A reduction of either sampling frequency or analog to digital resolution translates into less electrical current required to make and process each sensor sample. These benefits allow smaller and longer lasting implantable devices.

The discussion above has defined MEP's distributed computations and has illustrated how the derived parameters can be used in an implantable cardiac device as shown in FIG. 1. MEP parameters, unlike specific time parameters such as pre-ejection period (PEP), are not exclusively linked to specific components of the cardiac cycle, such as isovolumic contraction. Rather, they are an integrated property of anatomic and physiologic actions over a cardiac cycle.

As a result of distributing its computations over the cardiac cycle, MEP is well suited to assess if there is sufficient time for the entire sequence of systolic and diastolic events to take place or if the cardiac cycle time is too short. If one fixes the level of exertion and autonomic nervous system stimulation, the time required for systole (e.g. TIM) is observed to be fairly constant. Inappropriate increases in heart rate result in diastole becoming too short to adequately fill the heart for subsequent contractions. The cardiac cycle's duration when at the verge of inadequate diastole is referred to by Spinelli as Total Active Time or TAT.

The reduction of cardiac interval during exertion, an appropriate physiologic tachycardia, is accompanied by similar reductions of both systole, TIM, and diastole by virtue of the sympathetic part of the autonomic nervous system. On the other hand, pathologic tachycardias of either paced or intrinsic origin are not accompanied by ANS shortening of systole or TIM causing an abbreviated diastole to occur late in the cardiac cycle. The mechanical, elastic, inertial, intracardiac volume, and wall tension changes associated with systolic contraction and ejection thus appear relatively later in the cardiac cycle. As a result, MEP-phase of the impedance signal, which depends on all of these, is increased.

Figure 12:
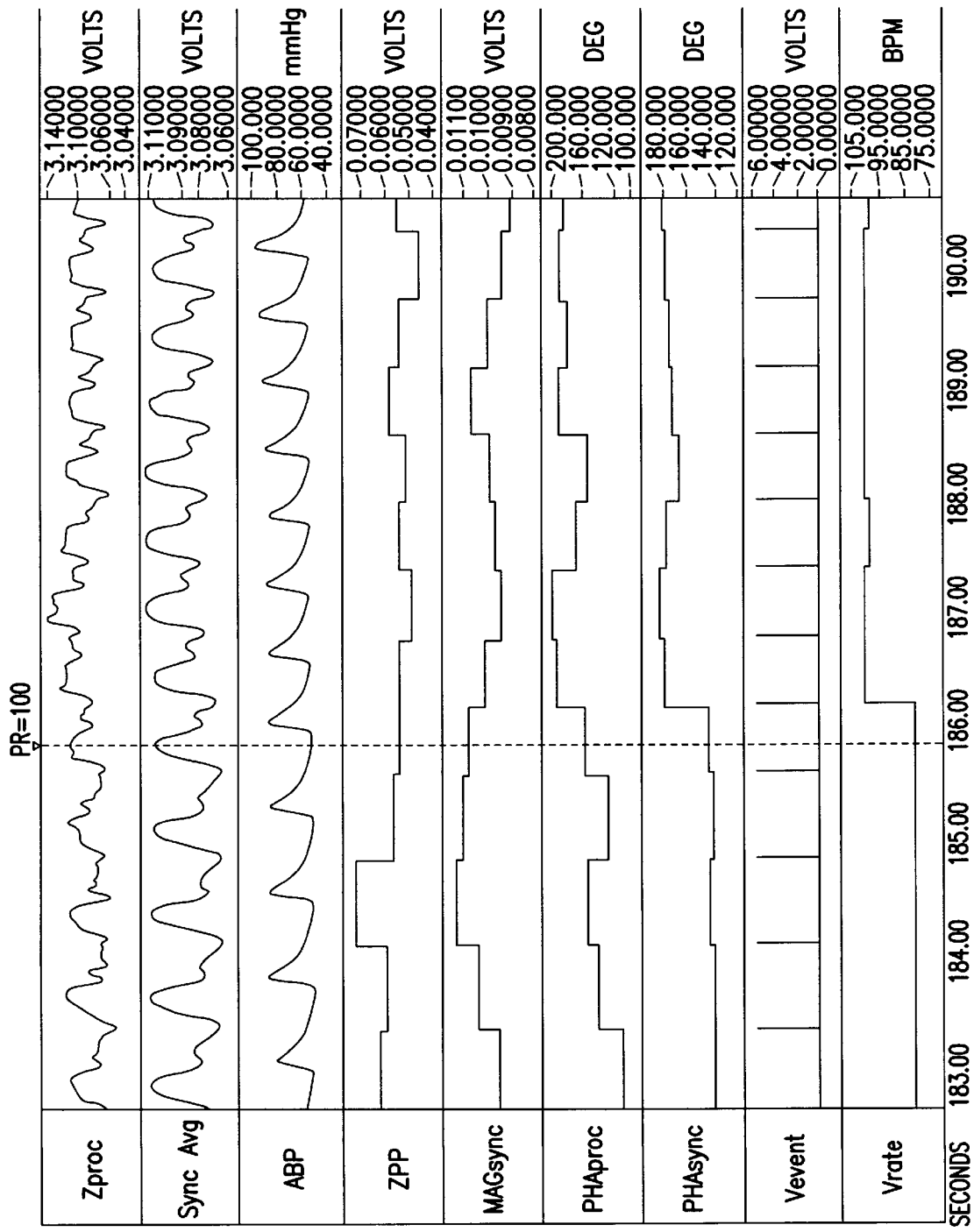
FIG. 12 is a series of plots which demonstrate an experimentally derived response which shows a step response in pacing rate and the benefits of synchronous averaging and MEP processing in accordance with this invention.

An example of a strong contribution of synchronous averaging to sensor signal processing is shown in FIG. 12. The actual impedance signal, after blanking and padding for pacing artifacts, appears in the top panel, $Z_{proc}$. At the lower pacing rate of 80 bpm, $Z_{proc}$ is fairly classical in shape but alters into a flat topped signal after the rate increases to 100 bpm. The synchronously averaged sensor signal, $Z_{sync}$, in the second panel, was derived from Equation 5 above and provides a responsive rendering of consistent changes to the sensor waveform. A clear rate-associated parameter change is seen in MEP-phase but is better defined when derived from $Z_{sync}$ ($PHA_{sync}$) instead of $Z_{proc}$ ($PHA_{proc}$). Note the almost step-like rise from 135° to 175° in the panel labeled $PHA_{sync}$. Parameters of this quality are necessary for stable rate limit and control algorithms.

A pair of symbolic diagrams (FIGS. 13a and 13b) show the essential distinction between the physiologic responses of MEP-phase and PEP, a more conventional time based parameter. As described above, PHA indicates directly a discrepancy between appropriate and inappropriate rates. By comparison, PEP and TIM reflect the autonomic nervous system's activity and physiologic demand.

FIG. 13a is a diagram of the response of MEP phase (PHA) to two hypothetical conditions under which heart rate may be increased. Under the condition of exercise and sympathetic autonomic nervous system (ANS) stimulation, both systole and diastole shorten, usually to a similar degree. As a result, although the frequency increases, the phase of the signal remains nearly constant at its normal baseline level. In contrast, pacing in the absence of metabolic demand (as well as pathologic tachycardias) creates a situation in which PHA increases since diastole is primarily shortened. One of the assets of PHA is that it directly indicates a discrepancy between appropriate and inappropriate rates in a variety of circumstances. It may thus be used directly in rate limiting and control algorithms to direct changes in therapeutic stimulation when, for example, it exceeds a threshold level.

In FIG. 13b, a conventional autonomic nervous system responsive variable such as PEP is shown to help compare with PHA in FIG. 13a. PEP (even when robustly resolved) reflects the ANS activity and demand. As such, it is useful in algorithms as an activity sensor surrogate or check, but is not immediately helpful in moment-to-moment pacing rate determination, since when exertion is fixed and pacing rate changes, PEP does not change significantly in response. The fact that PEP is greater or less than some threshold does not necessarily means that the pacing rate is inappropriately fast or slow.

Coordinate System Issues

There is an arbitrariness to the MEP-phase coordinate system regarding the order and sign of the arguments to the atan2() function of Equation 4. A preferred coordinate system usually assigns a positive angular values of 90° to 120° under normal sinus rhythm and normal low rates. This coincides with an impedance signal peak about ¼ to ⅓ of the way through the cardiac cycle. Under excessively high paced rates or pathologic tachycardias, the values may exceed 300°. Occasionally, in these same circumstances, the PHA values may exceed 360° when the impedance peak occurs later than the next ventricular paced or sensed event. Since phase is circular and wraps at 360°, it may be unwrapped to extend to values greater than 360° by any of a variety of methods such as past history or rate criteria.

Comparisons or computations based on MEP-phase need to be implemented either with the unwrapped value or interpreted modulo $2\pi$ or 360° to avoid radically different responses. As an example, assume that the rate algorithm's threshold or setpoint is 320° and that the measured phase is from 358° to 2°. We must respond to any phase in that interval with a response appropriate to a discrepancy which is high by 38–42°, and not one which is low by about 318°–320°.

Figure 15:
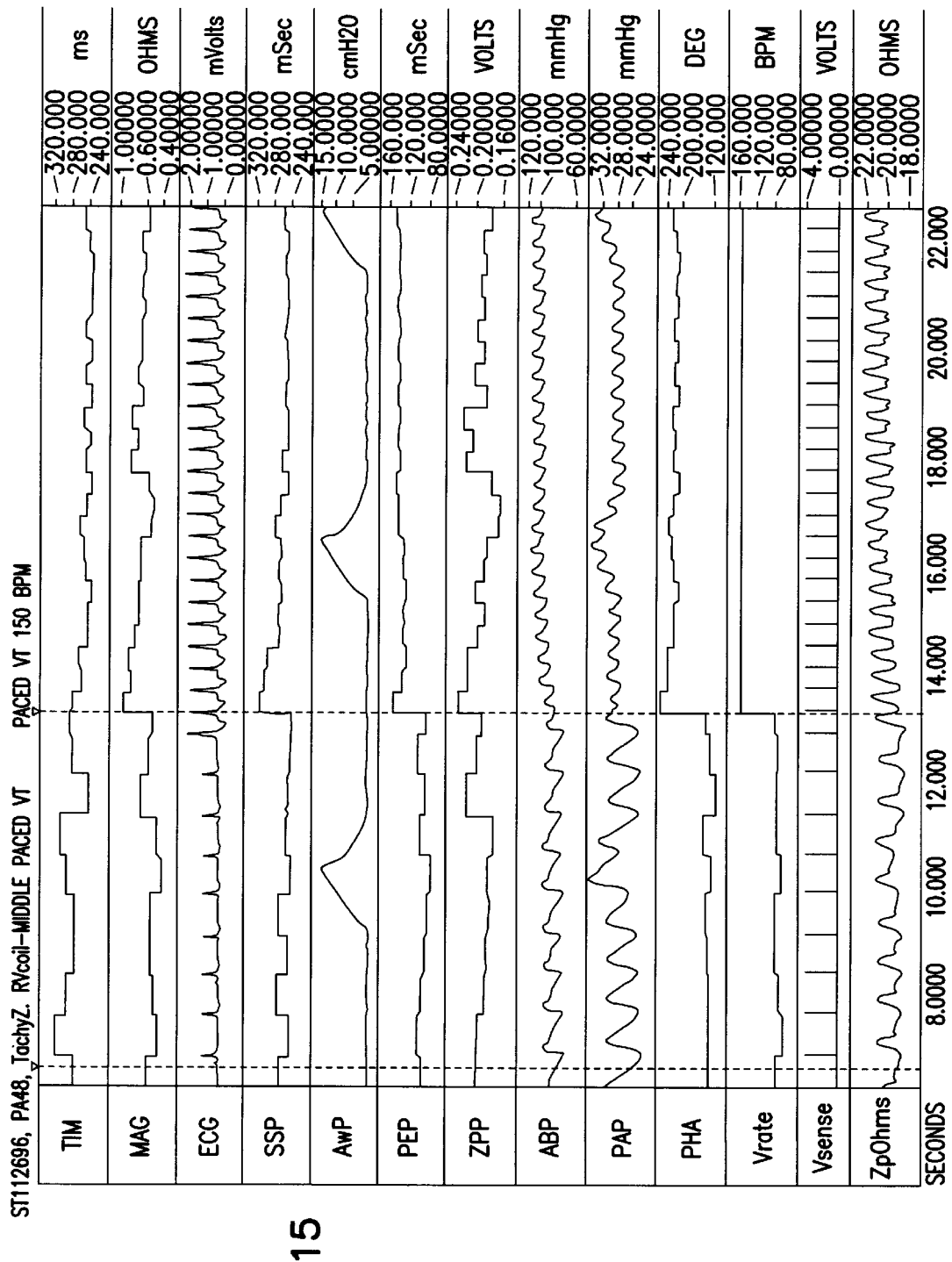
FIG. 15 is a series of plots demonstrating the application of this invention in detecting and responding to the onset of a potentially significant tachycardia.

With this in mind, refer now to FIG. 15. FIG. 15 depicts a series of traces for sudden onset of pacing simulated ventricular tachycardia at 150 bpm from a sinus rhythm baseline of 80 bpm. In this case, the moderate rate tachycardia is physiologically tolerated, judging from the traces for arterial blood pressure, ABP, and pulmonary artery pressure, PAP. FIG. 15 also shows MEP-TIM, MEP-MAG, and MEP-PHA. PHA increases dramatically from about 125° to about 220°. In contrast, PEP shows a paradoxical rise but TIM reveals a small decrease in the direction expected by ANS response. The fact that PHA remains just over 200° suggests, independent of pressure or flow, that there is just sufficient time in the cardiac cycle for diastole. This information is useful to determine that therapy might be withheld, at least initially, and thus serves to discriminate tolerable tachycardias.

This information is also useful in the event of an intolerable tachycardia. By setting predetermined levels for MEP parameters, particularly MEP PHA, and comparing the predetermined phase with the phase of the impedance signal, then the system of this invention may initiate antitachycardia therapies including burst pacing or defibrillation shocks. The system may also be adapted to compare the predetermined phase with the phase of the impedance or other sensor signal while pacing at a rate or timing distinct from the intrinsic rate or a safety pacing pulse to assess pacing capture and adjust the pacing output pulse amplitude accordingly.

Figure 16:
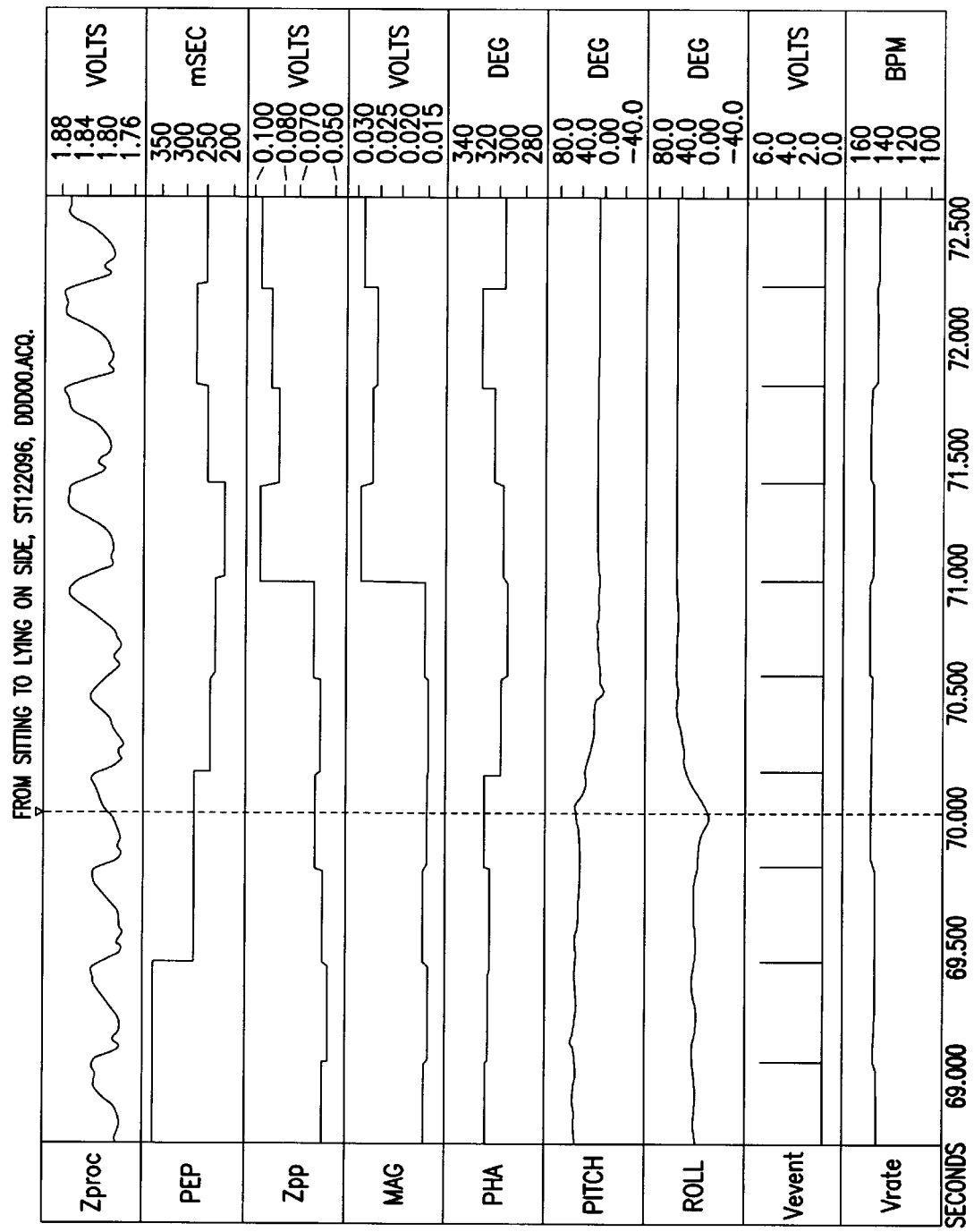
FIG. 16 is a series of plots showing MEP-phase insensitivity to a postural change of the intracardiac impedance signal at constant heart rate, and example of an event which is difficult to handle in known systems.

FIG. 16 depicts yet another advantageous feature of this invention. In this case, the subject changed posture from sitting to lying on his side, and the MEP-phase remained insensitive to this change in posture. Note that the peak-to-peak impedance signal, $Z_{pp}$, and MEP-MAG parameter nearly doubles in value, and that PEP is unreliable, but the PHA parameter remains almost constant at 300°.

Figure 17:
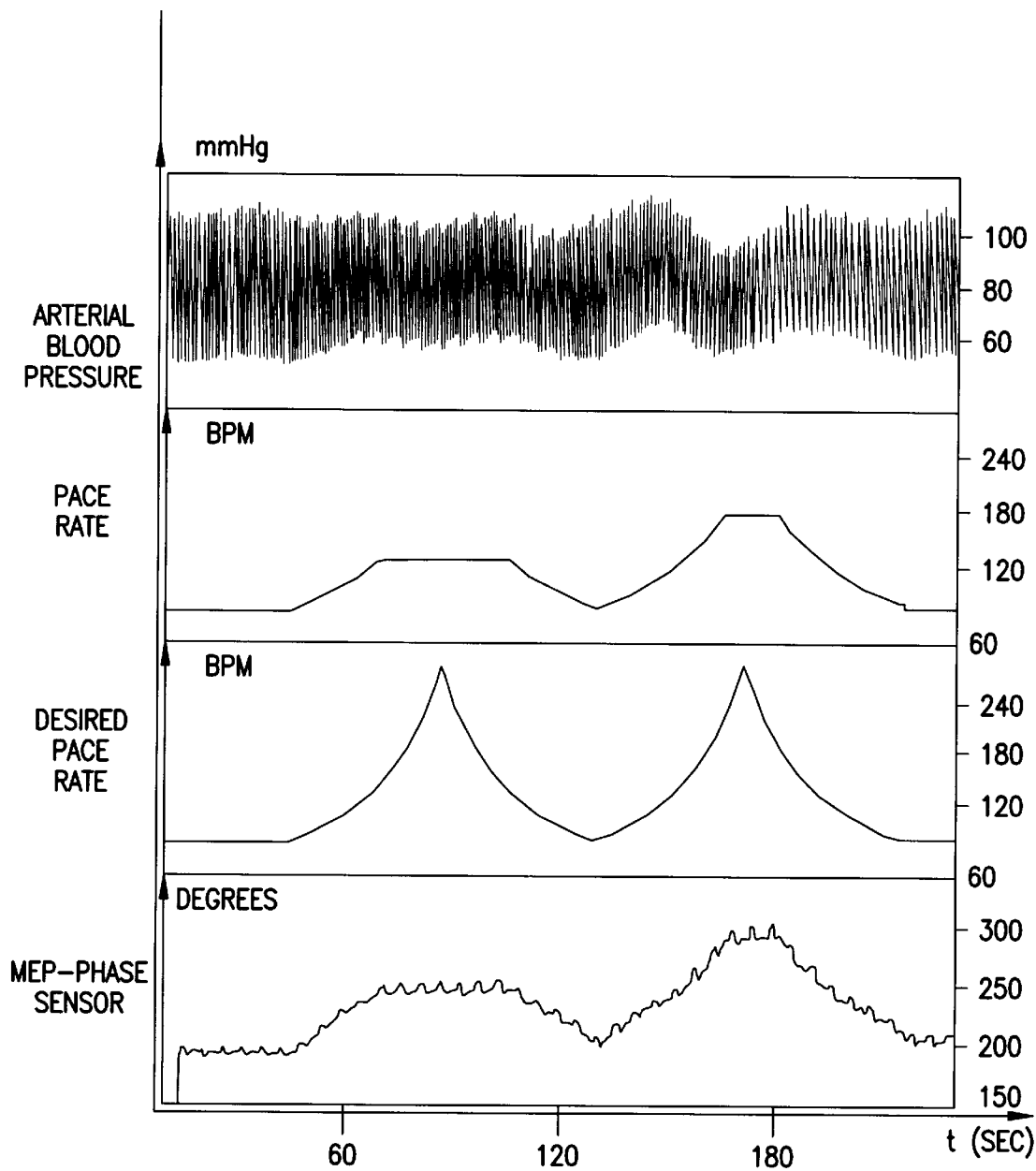
FIG. 17 is a series of plots demonstrating the usefulness of this invention in providing a physiologic upper limit on the pacing rate.

Finally, the present invention is also useful in governing the upper pacing rate, as shown in FIG. 17. This figure depicts an example of a pacing rate upper limit governed by MEP-phase. At a fixed workload or level of autonomic nervous system activity, PHA is closely tied to the actual pacing rate (compare pace rate with sensor signal in FIG. 17). In this case, a desired pacing rate trajectory, which extends from 100 to 300 bpm is dynamically limited to about 130 bpm and 180 bpm as a result of phase limits set at 248° and 301°, respectively. Arterial blood pressure is not seriously affected until the MEP-phase exceeds 280°. Note the effect on blood pressure at about 180 seconds with MEP-phase limit set at 301°. Thus, the quality of this parameter permits simple rate limiting algorithms which can dynamically readjust the upper limit as the subject accommodates.

Basis Function Extensions

An extension to better piecewise constant approximations to sine and cosine basis functions can be made either by extra accumulators with additional logic to catch just the regions near the sine and cosine peaks, or from the array of partial sums with subtractions again. More ideal versions of sine and cosine are preferred if the sensor signal contains high harmonics and sharp edges. However, since the square-wave sine and cosine consist only of odd harmonics weighted by 1/f, there is likely to be little benefit extending this past one additional level of approximation. The technique described above with regard to FIG. 9 is most flexible with regard to basis function implementations. Harmonics other than the fundamental may also be sought in this manner from a sensor signal by using basis functions which repeat over the cardiac cycle. Furthermore, nonsinusoidal basis functions may be employed to capitalize on information in a specific sensor signal.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

We claim:

1. A method of controlling the pacing rate of a cardiac pacemaker comprising the steps of:
    a. receiving a sensor signal waveform from a sensor lead of a pacemaker,
    b. deriving data from the sensor signal waveform, the derived data descriptive of the sensor signal waveform over at least most of a cardiac cycle,
    c. developing a first order parameter of the sensor signal waveform which defines that cardiac cycle, and
    d. providing the first order parameter to a microprocessor for control of a pacing signal of the cardiac pacemaker.

2. The method of claim 1, wherein the sensor is an impedance sensor.

3. The method of claim 1 further comprising the step of digitizing the sensor signal waveform prior to the step of deriving data from the sensor signal waveform.

4. The method of claim 1 wherein the first order parameter of the sensor signal waveform comprises the phase of the sensor signal waveform relative to a pacemaker or electrogram clock.

5. The method of claim 1 wherein the first order parameter of the sensor signal waveform comprises the mean of the sensor signal waveform.

6. The method of claim 1 wherein the first order parameter of the sensor signal waveform comprises the magnitude of the sensor signal waveform.

7. The method of claim 1 wherein the first order parameter of the sensor signal waveform comprises the period of the sensor signal waveform.

8. The method of claim 1 wherein the first order parameter of the sensor signal waveform comprises a time parameter of the sensor signal waveform relative to a pacemaker or electrogram clock.

9. The method of claim 1 wherein the step of developing a first order parameter of the sensor signal waveform comprises developing a composite first order parameter of the sensor signal waveform from a function of the mean, magnitude, phase, period, and time parameters of the sensor signal waveform.

10. The method of claim 1 wherein the step of deriving data from the sensor signal waveform further comprises the step of decomposing the sensor signal waveform into sine and cosine basis function components.

11. The method of claim 1 wherein the step of deriving data from the sensor signal waveform further comprises the step of developing a piecewise constant approximation of the sine and cosine components of the sensor signal waveform.

12. A device for controlling the pacing rate of a cardiac pacemaker comprising:
    a. means for receiving a sensor signal waveform from a sensor lead of a pacemaker,
    b. means for deriving data from the sensor signal waveform, the derived data descriptive of the sensor signal waveform over at least most of a cardiac cycle,
    c. means for developing a first order parameter of the sensor signal waveform which defines that cardiac cycle, and
    d. means for providing the first order parameter to a microprocessor for control of a pacing signal of the cardiac pacemaker.

13. The device of claim 12, further comprising means for digitizing the sensor signal waveform.

14. The device of claim 12, further comprising means for decomposing the sensor signal waveform into basis functions, the means for decomposing providing basis functions to the means for developing a first order parameter.

15. The device of claim 12, further comprising means for decomposing the sensor signal waveform into sine and cosine basis functions, the means for decomposing providing basis functions to the means for developing a first order parameter.

16. The device of claim 12, further comprising means for decomposing the sensor signal waveform into sine-square and cosine-square basis functions, the means for decomposing providing basis functions to the means for developing a first order parameter.

17. The device of claim 12, further comprising means for developing a piecewise constant approximation of the sine and cosine components of the sensor signal waveform, the means for developing a piecewise constant approximation providing values to the means for developing a first order parameter.

18. A cardiac stimulation apparatus comprising:
   a. a stimulus generator for stimulating a patient's heart;
   b. a sensor adapted to be coupled to the patient's heart for sensing a time varying physiologic characteristic of the heart,
   c. a signal injector for impressing a signal, on the heart which develops the signal detected by the sensor;
   d. an extractor coupled to the signal injector, the extractor generating a first order parameter of the time varying characteristic of the heart based upon at least most of a cardiac cycle, and
   e. a microprocessor to receive the first order parameter and activate a pacing pulse from the stimulus generator based on the first order parameter.

19. A method of controlling the pacing rate of a cardiac pacemaker comprising the steps of:
   a. sensing an impedance of a region of a heart with a sensor lead of a pacemaker, resulting in an impedance signal,
   b. sampling the impedance signal, resulting in a digitized impedance signal,
   c. blanking and padding the digitized impedance signal, resulting in a filtered impedance signal,
   d. synchronous averaging the filtered impedance signal, resulting in a synchronous averaged impedance signal,
   e. extracting a first order parameter from the synchronous averaged impedance signal,
   f. providing the first order parameter to a microprocessor for control of a pacing signal of the cardiac pacemaker.

20. The method of claim 19, wherein the step of extracting a first order parameter includes the steps of:
   a. providing the synchronous averaged impedance signal and an event trigger signal to a processor,
   b. continuously updating a first set of registers in the processor, the first set of registers storing a set of values representative of the synchronous averaged impedance signal,
   c. once each cardiac cycle, outputting the values in the first set of registers to a second set of registers, the second set of registers storing values representative of substantially all of a cardiac cycle, and
   d. calculating a first order parameter from the values stored in the second set of registers.

21. The method of claim 20, wherein the first order parameter comprises the phase of the impedance signal.

22. The method of claim 21, further comprising the step of storing in the microprocessor a predetermined phase for comparison with the phase of the impedance signal.

23. The method of claim 22, further comprising the step of comparing the predetermined phase with the phase of the impedance signal and thereby determining the pacing rate of the cardiac pacemaker.

24. The method of claim 22, further comprising the step of comparing the predetermined phase with the phase of the impedance signal and thereby limiting the pacing rate of the cardiac pacemaker.

25. The method of claim 22, further comprising the step of comparing the predetermined phase with the phase of the impedance signal and thereby initiating antitachycardia therapies including burst pacing or defibrillation shocks.

26. The method of claim 22, further comprising the step of comparing the predetermined phase with the phase of the impedance signal while pacing at a rate or timing distinct from the safety pulse or intrinsic rate to assess pacing capture and adjust pacing output pulse amplitude accordingly.

27. A method of controlling the pacing rate of a cardiac pacemaker comprising the steps of:
   a. sensing an impedance of a region of a heart with a sensor lead of a pacemaker, resulting in an impedance signal,
   b. sampling the impedance signal, resulting in a digitized impedance signal,
   c. blanking and padding the digitized impedance signal, resulting in a filtered impedance signal,
   d. synchronous averaging the filtered impedance signal, resulting in a synchronous averaged impedance signal,
   e. extracting a harmonic of a first order parameter from the synchronous averaged impedance signal,
   f. providing the harmonic of the first order parameter to a microprocessor for control of a pacing signal of the cardiac pacemaker.

* * * * *

UNITED STATES PATENT AND TRADEMARK OFFICE
CERTIFICATE OF CORRECTION

PATENT NO.: 5,999,854

DATED: Dec. 7, 1999

INVENTOR(S): Deno et al.

It is certified that error appears in the above-identified patent and that said Letters Patent is hereby corrected as shown below:

In the Inventor field [75], please insert --, both of Tex.-- after "Alec Vautravers, Houston".

In the Inventor field [75], please insert --, Colo.-- after "Arvada".

In the Inventor field [75], please delete "all of" in the last line.

In column 9, line 1, please delete "C" and insert --T--, therefore.

Signed and Sealed this

Tenth Day of April, 2001

Attest:

NICHOLAS P. GODICI

Attesting Officer    *Acting Director of the United States Patent and Trademark Office*